(12) United States Patent
Kamei et al.

(10) Patent No.: US 7,635,714 B2
(45) Date of Patent: Dec. 22, 2009

(54) METHODS OF TREATING DYSCHEZIA

(75) Inventors: Kenshi Kamei, Gotenba (JP); Hirokazu Sudo, Gotenba (JP); Kenichi Ozaki, Gotenba (JP); Osamu Cynshi, Gotenba (JP); Hideki Sato, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 44 days.

(21) Appl. No.: 10/532,585

(22) PCT Filed: Oct. 24, 2003

(86) PCT No.: PCT/JP03/13627

§ 371 (c)(1),
(2), (4) Date: Apr. 25, 2005

(87) PCT Pub. No.: WO2004/037273

PCT Pub. Date: May 6, 2004

(65) Prior Publication Data
US 2006/0014706 A1 Jan. 19, 2006

(30) Foreign Application Priority Data
Oct. 25, 2002 (JP) ............................ 2002-311284

(51) Int. Cl.
*A61K 31/335* (2006.01)
*A61K 31/351* (2006.01)
(52) U.S. Cl. .................................. 514/450
(58) Field of Classification Search ............ None
See application file for complete search history.

(56) References Cited

U.S. PATENT DOCUMENTS 6,562,795 B2 * 5/2003 Ashley et al. .............. 514/29

FOREIGN PATENT DOCUMENTS

| EP | 1314737 A1 | 5/2003 |
|---|---|---|
| JP | 2001-119295 | 4/2000 |
| WO | WO 93/13780 A1 | 7/1993 |
| WO | WO 97/31930 A1 | 9/1997 |
| WO | WO 98/03531 | 1/1998 |
| WO | WO 00/09530 A1 | 2/2000 |
| WO | WO 01/60833 A2 | 8/2001 |
| WO | WO 02/018403 A1 | 7/2002 |

OTHER PUBLICATIONS

The Merck Manual, 17th edition, p. 283.*
Peeters, T.L., Current Opinion in Investigational Drugs, 2(4), (2001), 555-557 (abstract).*
Clark et al., Clinical and Experimental Pharmacology and Physiology (1999) 26, 242-245.*
Dtsch. Z. Verdau Stoffwechselkr, (1986); 46(2):122-9 (abstract).*
Miller et al., Peptides, 21 (2000) 283-287.*

O. Alaradi et al; "Irritable bowel syndrome: update on pathogenesis and management"; *Med Principles Pract*; vol. 11, p. 2-17, 2002.
M. Bradette, et al; "Effect of motilin and erythromycin on the motor activity of the human colon"; *J. Gastrointest. Mot.*, vol. 5, pp. 247-251, 1993.
D. M. Chieppa, et al; Effects of erythromycin on human colonic circular muscle in idiopathic chronic constipation, *European Journal of Clinical Investigation*; vol. 30, pp. 66-71, 2000.
D. Harari et al; "Correlates of regular laxative use by frail elderly persons"; *The American Journal of Medicine*, vol. 99, pp. 513-518.
Zen Itoh; "Motilin and Clinical Application"; *Peptides*, vol. 18, No. 4, pp. 593-608, 1997.
J. S. Jameson et al; "Oral or intravenous erythromycin has no effect on human distal colonic motility"; *Aliment, Pharmacol. Ther.*, vol. 6, pp. 589-595, 1992.
I.M.C. Kamerling et al; "Dose-related effects of motilin on proximal gastrointestinal motility"; *Ailment Pharmacol Ther*; vol. 16, pp. 129-135, 2002.
I.M.C. Kamerling et al; "Exogenous motilin affects postprandial proximal gastric motor function and visceral sensation"; *Digestive Diseases and Sciences*; vol. 47, No. 8, pp. 1732-1736, 2002.
H. Koga et al; "Design, SAR and pharmacology of GM-611, the first acid-stable non-peptide motilin receptor agonist"; *Drugs of the Future*; vol. 27, No. 3; pp. 255-272, 2002.
Y.C. Luiking et al; "Motilin induces gall bladder emptying and antral contractions in the fasted state in humans"; *Gut*; vol. 42, pp. 830-835, 1998.
M. Pappagallo: "Incidence, Prevalence, and Management of Opioid Bowel Dysfunction"; *The American Journal of Surgery*; vol. 182, pp. 11S-18S; 2001.
S. Sharma et al "Effect of oral erythromycin on colonic transit in patients with idiopathic constipation"; *Digestive Diseases and Sciences*, vol. 40, No. 11, pp. 2446-2449, 1995.
D. Thorpe; "Management of Opioid-induced Constipation"; *Curr. Pain Headache Rep.*, vol. 5, pp. 237-240, 2001.

* cited by examiner

*Primary Examiner*—Phyllis G. Spivack
(74) *Attorney, Agent, or Firm*—Browdy & Neimark, PLLC

(57) ABSTRACT

A compound of Formula (1) or a pharmaceutically acceptable salt thereof:

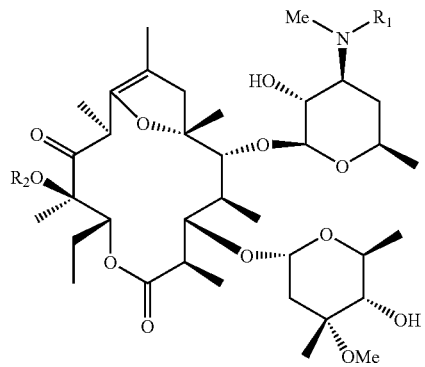

wherein $R_1$ represents a $C_1$-$C_6$ alkyl group and $R_2$ represents a $C_1$-$C_6$ alkyl group, while unlike a laxative, is effective in the treatment of constipation.

6 Claims, 7 Drawing Sheets

METHODS OF TREATING DYSCHEZIA

TECHNICAL FIELD

The present invention relates to a therapeutic and/or preventive agent for defecation dysfunction, which comprises an erythromycin derivative as an active ingredient, as well as a method for treating and/or preventing defecation dysfunction, which comprises administering an effective dose of the therapeutic and/or preventive agent to patients.

BACKGROUND ART

Defecation is a physiological action essential to human life. Dysfunction in defecation causes symptoms of constipation and significantly reduces QOL. Constipation is a generic term for symptoms of defecation trouble associated not only with decreased frequency and/or amount of defecation, but also with changed condition of stool, incomplete evacuation and hypogastric flatulence. Constipation is caused by a variety of factors, including lack of food intake and exercise. In addition to these factors, every year there is an increasing number of constipation cases caused by other factors, for example, constipation associated with aging and social stress, analgesic-induced constipation caused by, e.g., morphine used in cancer treatment and surgical operation, and functional constipation (e.g., constipation associated with irritable bowel syndrome, atonic constipation, rectal constipation, chronic constipation). To treat these types of constipation, patients usually receive education on lifestyle habits to do with diet and exercise along with a laxative for medical treatment. However, a laxative is associated with a problem of frequent diarrhea and/or abdominal pain as side effects although treatment with a laxative may produce a transient improvement in symptoms. In patients with chronic constipation, continuous medication is desired because the symptoms become worse immediately upon interruption of medication; but a laxative is more likely to induce drug resistance in a patient with continuous medication and it may eventually lose its efficacy.

In addition to a laxative, a gastroprokinetic agent such as cisapride may be used for treating constipation. Such an agent is considered to relieve constipation through enhancement of colonic motility. However, agents of this type have serious side effects including neurological effects, as represented by the fact that cisapride was withdrawn from the market because it was suspected to cause sudden death due to QT prolongation.

As a strategy to avoid these side effects, gastrointestinal motility may be enhanced through receptors expressed exclusively in the gastrointestinal tract. The motilin receptor is a receptor for gastrointestinal motility hormone and this receptor is considered to be specifically distributed in the gastrointestinal tract. Motilin is known as a gastrointestinal motility hormone that is highly specific to the gastrointestinal tract. It is supposed that motilin stimulates upper gastrointestinal motility in human (see, e.g., Itoh Z. Motilin and clinical application. Peptides. 1997 18:593-608) and also reported not to affect colonic motility (Bradette M, Poitras P, Boivin M. Effect of motilin and erythromycin on the motor activity of the human colon. J Gastrointest Mot 1993 5:247-251). In addition, recent studies suggest the probability that motilin makes an indirect contribution to colonic motility in view of the fact that motilin stimulates acetylcholine-induced colonic contraction; but it is reported that motilin has no direct stimulatory effect on colonic contraction (Chieppa D M, Mansi G, Rinaldi R, Serio M, Nacci C, Montagnani M, Potenza M A, De Salvia M A, Mitolo C I, Rinaldi M, Altomare D F. Effects of erythromycin on human colonic circular muscle in idiopathic chronic constipation. Eur J Clin Invest. 2000 30:66-71). It is therefore unclear whether defecation can be accelerated by motilin or a motilin agonist. It is also reported that erythromycin, a motilin agonist, fails to enhance colonic motility (Jameson J S, Rogers J, Misiewicz J J, Raimundo A H, Henry M M, Oral or intravenous erythromycin has no effect on human distal colonic motility. Aliment Pharmacol Ther. 1992 6:589-95). On the other hand, it is reported that erythromycin relieves constipation (Sharma S S, Bhargava N, Mathur S C. Effect of oral erythromycin on colonic transit in patients with idiopathic constipation. A pilot study. Dig Dis Sci. 1995 40:2446-9). However, it is considered that the relief of constipation may be due to a synergistic effect between indirect enhancement of colonic motility and changes in enterobacterial flora induced by the antibacterial action of erythromycin; and hence, it is unclear whether constipation is relieved by a motilin agonist having a weak or no antibacterial action. In addition, because of its antibacterial action, erythromycin is clinically unsuitable for continuous medication as a therapeutic agent for constipation. Furthermore, in clinical studies, there is no report about an acceleratory effect on defecation by administration of motilin (see, e.g., Kamerling I M, van Haarst A D, Burggraaf J, de Kam M, Biemond I, Jones R, Cohen A F, Masclee A A. Exogenous motilin affects postprandial proximal gastric motor function and visceral sensation. Dig Dis Sci. 2002 47:1732-6; Kamerling I M, Van Haarst A D, Burggraaf J, Schoemaker H C, Biemond I, Jones R, Cohen A F, Masclee A A. Dose-related effects of motilin on proximal gastrointestinal motility. Aliment Pharmacol Ther. 2002 16:129-35; Luiking Y C, Peeters T L, Stolk M F, Nieuwenhuijs V B, Portincasa P, Depoortere I, van Berge Henegouwen G P, Akkermans L M. Motilin induces gall bladder emptying and antral contractions in the fasted state in humans. Gut. 1998 42:830-5).

Based on the above background, there is a need to develop a medicament that improves defecation functions by a different mechanism than a laxative, particularly relieves senile constipation, analgesic-induced constipation (e.g., morphine-induced constipation), and functional constipation (e.g., constipation associated with irritable bowel syndrome, atonic constipation, rectal constipation, chronic constipation). Since a laxative causes a large change in stool condition, it would give a great distress to patients and would not be effective for continuous medication. Also, it is reported that in patients with such constipation, existing agents including a laxative will not always lead to desired clinical effects such as improved QOL (Harari D, Gurwitz J H, Avorn J, Choodnovskiy I, Minaker K L. Correlates of regular laxative use by frail elderly persons. Am J Med. 1995 99:513-8; Pappagallo M. Incidence, prevalence, and management of opioid bowel dysfunction. Am J Surg. 2001 182:11S-18S; Thorpe D M. Management of opioid-induced constipation. Curr Pain Headache Rep. 2001 5:237-40; Alaradi O, Barkin J S. Irritable bowel syndrome: update on pathogenesis and management. Med Princ Pract. 2002 11:2-17). Under the circumstances, there is a need to provide an agent that facilitates normal defecation without changing stool condition and that continuously improves defecation functions.

On the other hand, JP 6-56843 A and WO93/24509 teach that a specific type of erythromycin derivative serves as a motilin agonist and enhances upper gastrointestinal motility. Moreover, among this type of compound, erythromycin, 8,9-didehydro-N-demethyl-9-deoxo-6,11-dideoxy-6,9-epoxy-12-O-methyl N-(1-methylethyl)-11-oxo-,(2E)-2-butenedioate (2:1) [development code: GM-611 (Chugai Pharmaceutical Co., Ltd.), hereinafter simply referred to as "GM-611"] is reported to have a weaker antibacterial action than erythromycin and hence suggested to be available for long-term clinical use (Koga H, Takanashi H, Itoh Z, Omura S. Design, SAR and pharmacology of GM-611, the first acid-stable nonpeptide motilin receptor agonist. Drugs Future. 2002 27:255-272). However, it is not known that these compounds have an improving effect on defecation functions, such as those leading to increased frequency and amount of defecation. Thus, as stated above, there is a need to provide a therapeutic and/or preventive agent for defecation dysfunction, which is suitable for continuous medication and acts by a different mechanism than a laxative.

DISCLOSURE OF THE INVENTION

As a result of extensive and intensive efforts made to overcome the problems stated above, the inventors of the present invention have found that a specific type of erythromycin derivative is preferred as a therapeutic and/or preventive agent for defecation dysfunction because it is capable of improving defecation functions and also suitable for continuous medication.

Namely, the present invention relates to a therapeutic and/or preventive agent for defecation dysfunction, which comprises as an active ingredient a compound of Formula (1) or a pharmaceutically acceptable salt thereof:

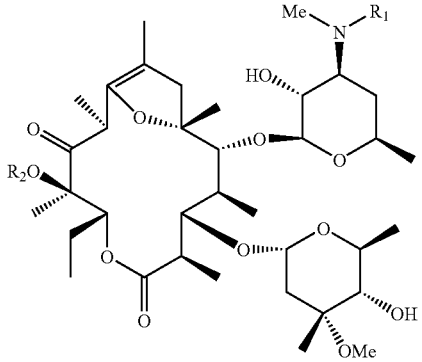

(wherein $R_1$ represents a $C_1$-$C_6$ alkyl group and $R_2$ represents a $C_1$-$C_6$ alkyl group).

Also, the present invention relates to a method for treating and/or preventing defecation dysfunction in a patient with defecation dysfunction, which comprises administering to the patient, a therapeutic and/or preventive agent for defecation dysfunction comprising as an active ingredient the above compound of Formula (1) or a pharmaceutically acceptable salt thereof, wherein the therapeutic and/or preventive agent is administered in doses sufficient to treat and/or prevent defecation dysfunction in the patient.

In a preferred embodiment for the above compound of Formula (1) used as an active ingredient in the present invention, $R_1$ in Formula (1) is an isopropyl group. In a more preferred embodiment, $R_2$ in Formula (1) is a methyl group.

In a preferred embodiment for defecation dysfunction targeted by the present invention, defecation dysfunction is constipation. In a more preferred embodiment, defecation dysfunction is selected from analgesic-induced constipation (e.g., morphine-induced constipation), functional constipation (e.g., constipation associated with irritable bowel syndrome, atonic constipation, rectal constipation, chronic constipation) and senile constipation.

The present invention will be further described in more detail.

In the compound of Formula (1) used as an active ingredient in the present invention, $R_1$ and $R_2$ each independently represent a $C_1$-$C_6$ alkyl group. As used herein, a $C_1$-$C_6$ alkyl group refers to a linear or branched alkyl group containing 1 to 6 carbon atoms. Specific examples include a methyl group, an ethyl group, an n-propyl group, an isopropyl group, an n-butyl group, an isobutyl group, a sec-butyl group, a tert-butyl group, a pentyl group, a neopentyl group and a hexyl group. Among them, preferred are linear or branched $C_1$-$C_3$ alkyl groups including a methyl group, an ethyl group, an n-propyl group and an isopropyl group. Particularly preferred examples of $R_1$ include an isopropyl group, while particularly preferred examples of $R_2$ include a methyl group.

The compound of Formula (1) may be in a salt form. Examples of possible salts include those with inorganic acids such as hydrochloric acid, hydrobromic acid, hydroiodic acid and sulfuric acid, as well as those with organic acids such as acetic acid, oxalic acid, maleic acid, fumaric acid and methanesulfonic acid, with a fumaric acid salt being preferred. Alternatively, the compound of Formula (1) may be in a hydrate form.

Preferred is a compound of Formula (1) wherein $R_1$ is an isopropyl group and $R_2$ is a methyl group, i.e., 8,9-didehydro-N-demethyl-9-deoxo-6,11-dideoxy-6,9-epoxy-12-O-methyl-N-(1-methylethyl)-11-oxoerythromycin. More preferred is a fumaric acid salt of the compound, i.e., erythromycin, 8,9-didehydro-N-demethyl-9-deoxo-6,11-dideoxy-6,9-epoxy-12-O-methyl N-(1-methylethyl)-11-oxo-, (2E)-2-butenedioate (2:1) [development code: GM-611 (Chugai Pharmaceutical Co., Ltd.), hereinafter simply referred to as "GM-611"].

The compound of Formula (1) used in the present invention is known and can be synthesized as described in, e.g., Bioorg & Med Chem Lett, Vol. 4, No. 11, page 1347, 1994; JP 6-56843 A (WO93/24509); JP 9-100291 A (WO97/06177); WO02/18403 or WO02/30943.

The target disease of the present invention is defecation dysfunction. Defecation dysfunction refers to a condition associated with decreased frequency and/or amount of defecation, regardless of its cause. More specifically, such a condition is intended to mean constipation. Constipation as used herein includes analgesic-induced constipation (e.g., morphine-induced constipation), functional constipation (e.g., constipation associated with irritable bowel syndrome, atonic constipation, rectal constipation) and senile constipation.

As used herein, the term "therapeutic and/or preventive agent" refers to an agent used for either or both treatment and prevention purposes. More preferably, this term refers to an agent used for treating and/or preventing the target disease stated above or inhibiting the disease from progressing to more advanced stages so as to prevent further deterioration and/or maintain the status quo.

The therapeutic and/or preventive agent for defecation dysfunction according to the present invention preferably facilitates normal defecation. As used herein, the term "normal defecation" means that defecation occurs without changing stool condition for the worse, without increasing the water content of stool, or without changing stool into a diarrheal form.

The pharmaceutical composition of the present invention may be prepared in various dosage forms by mixing the compound of Formula (1) as an active ingredient with a physiologically acceptable solid or liquid pharmaceutical carrier as appropriate for the intended route of administration.

Possible routes of administration include oral administration, parenteral administration (e.g., intravenous injection), sustained release-administration using sustained-release preparations, and local administration using local delivery catheters or the like. Pharmaceutical carriers include commonly used excipients, binders, disintegrating agents, lubricants, coating agents, solubilizers, emulsifiers, suspending agents, stabilizers, fats/oils, and solvents. Dosage forms include tablets, granules, pills, capsules, solutions, syrups, suspensions, emulsions and injections.

Although the dose of a compound of Formula (1) according to the present invention may be selected as appropriate for the age of a patient, the type of disease to be treated, the severity of symptoms, the intended route of administration and so on, the daily dose for adults may be 1 to 1000 mg, preferably 5 to 400 mg. More specifically, when administered with a particularly preferred compound GM-611, an adult patient preferably receives 10 mg to 40 mg of the compound, which may be given in single or divided doses.

When a subject is administered with the therapeutic and/or preventive agent for defecation dysfunction according to the present invention, some characteristic effects are observed in the subject. For example, after a compound of Formula (1), including GM-611, is administered in a therapeutically or preventively effective dose, the administered subject shows activation of the upper gastrointestinal motility, as well as enhancement of colonic motility. Also, the starting point of GMC (giant migrating contraction) in the colon is closer to the mouth when compared to normal defecation; and in some cases, GMC is observed to occur starting from the ileum. Moreover, in defecation following administration of the therapeutic and/or preventive agent of the present invention, there are increases in the frequency of GMC and in the amount of a single defecation, and also the interval between defecations shows a tendency to increase. These effects will also contribute to the intended clinical effects such as improved QOL, particularly the improving effect on defecation functions without giving any distress on subjects to be administered.

EXAMPLES

Figure 1:
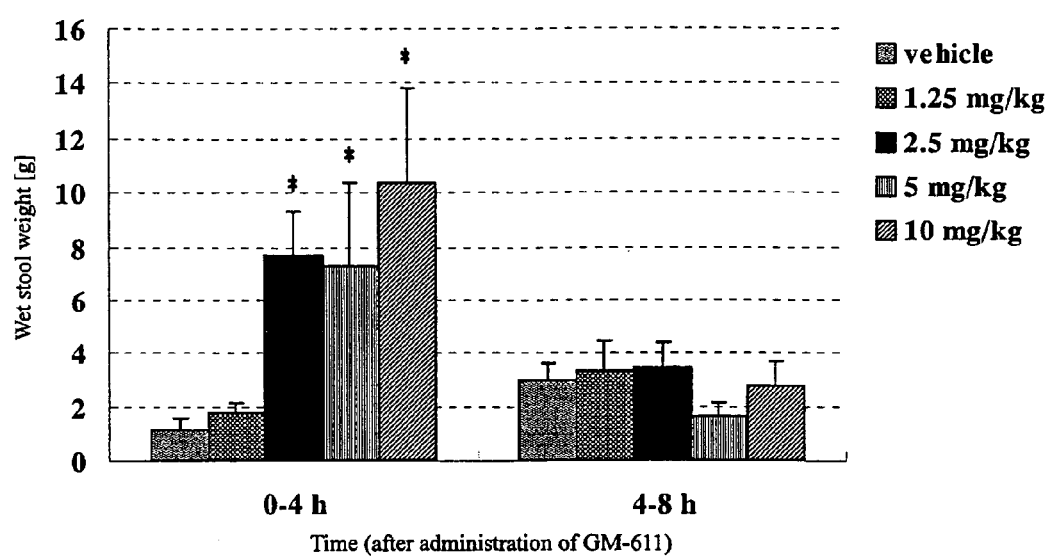
FIG. 1 shows an example of the results, in which the stool weight was measured for each normal rabbit administered with the therapeutic and/or preventive agent for defecation dysfunction according to the present invention.

The present invention will be further described in more detail by reference to the following examples, which are not intended to limit the scope of the invention.

In the following examples, GM-611 (erythromycin, 8,9-didehydro-N-demethyl-9-deoxo-6,11-dideoxy-6,9-epoxy-12-O-methyl N-(1-methylethyl)-11-oxo-, (2E)-2-butenedioate (2:1)) was used as a compound of Formula (1). This compound was synthesized in the laboratory of Chugai Pharmaceutical Co., Ltd. as described in WO02/18403 and WO02/30943.

Example 1

Acceleratory Effects of GM-611 on Defecation in Normal Rabbits

To study the difference of effects between GM-611 and a laxative, sennoside (sennoside solution (trade name), Taisho Pharm. Ind., Ltd.) was used as a laxative to compare with acceleratory effects of GM-611 on defecation. More specifically, normal rabbits were orally administered with GM-611 or sennoside and then measured for the weight and water content of stools. Normal rabbits (Kbl:JW), in groups of 13 to 15, were orally administered with vehicle (3 w/v % gum arabic suspension), GM-611 (1.25 mg/kg, 2.5 mg/kg, 5 mg/kg, 10 mg/kg), vehicle (purified water), or sennoside (12 mg/kg, 24 mg/kg, 48 mg/kg). The stool weight was then measured every 4 hours until 8 hours after administration. Also, their stools were collected, dried in a dry oven (at 120° C. for 24 hours or longer) and then the dry stool weight was measured to calculate the water content of stools (%) according to the following formula: ((wet stool weight [g]−dry stool weight [g]))/wet stool weight [g])×100.

[Results]

Figure 2:
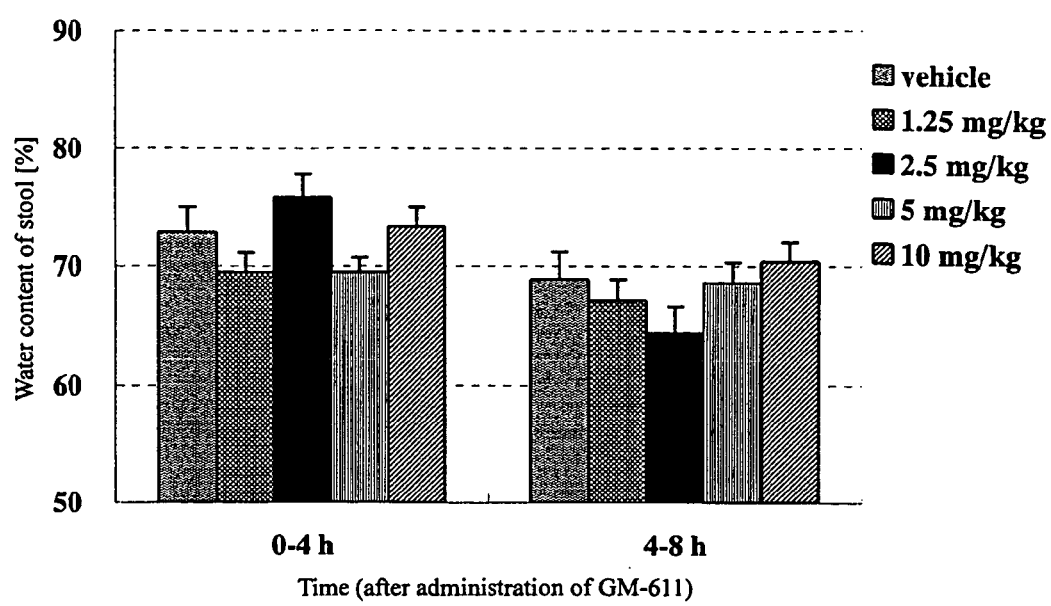
FIG. 2 shows an example of the results, in which the water content of stool was measured for each normal rabbit administered with the therapeutic and/or preventive agent for defecation dysfunction according to the present invention.
Figure 3:
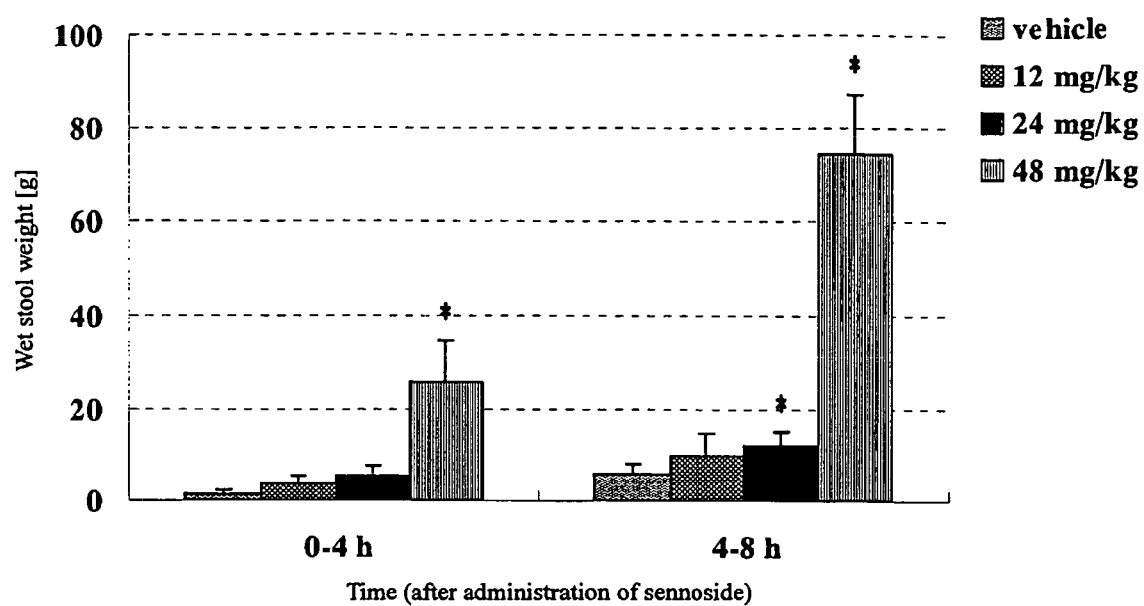
FIG. 3 shows an example of the results, in which the stool weight was measured for each normal rabbit administered with a laxative sennoside (positive control).
Figure 4:
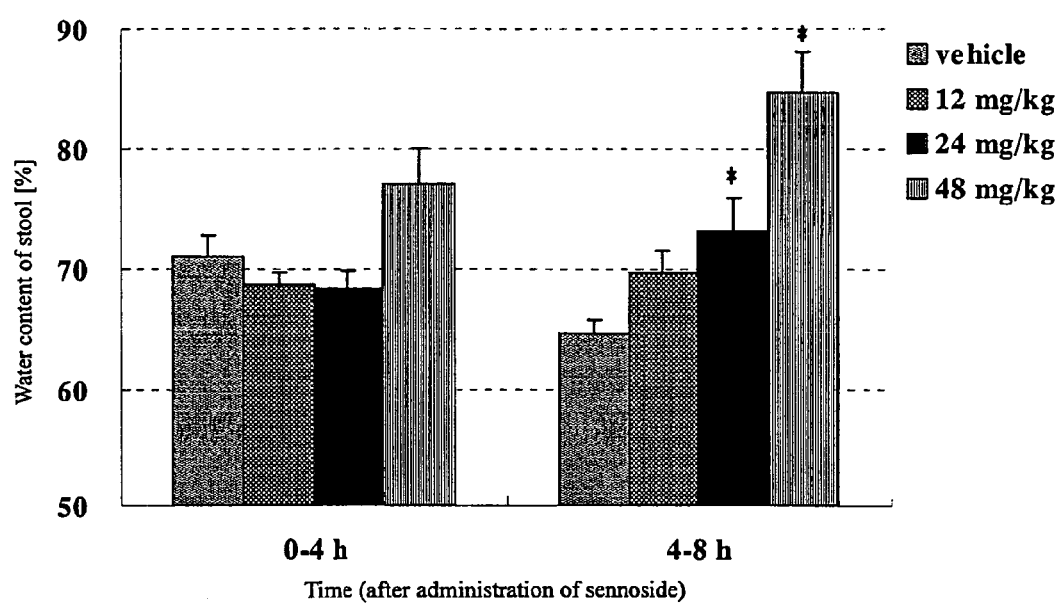
FIG. 4 shows an example of the results, in which the water content of stools was measured for each normal rabbit administered with a laxative sennoside (positive control).

GM-611 dose-dependently increased in the stool weight during 0 to 4 hours after administration (FIG. 1; *P<0.05 vs vehicle group by Shirley-Williams' test, n=13), but caused no change in the water content of stool (FIG. 2; n=10-13). Sennoside also dose-dependently increased in the stool weight, but this increase tended to be delayed (significantly observed during 4 to 8 hours after administration) (FIG. 3; *P<0.05 vs vehicle group by Shirley-Williams' test, n=13-15). In the sennoside-treated groups, the water content of stools was also increased dose-dependently (FIG. 4; *P<0.05 vs vehicle group by Dunnett's test, n=8-15). These results indicated that sennoside accelerated defecation with increasing water content of stools, i.e., defecation with diarrhea, whereas GM-611 accelerated normal defecation without increasing water content of stools.

Example 2

Improving Effect of GM-611 on Morphine-Induced Defecation Dysfunction

Effects on defecation dysfunction can be studied using an animal model with morphine-induced defecation dysfunction. To study the effect of GM-611 on defecation dysfunction, rabbits were subcutaneously administered with morphine (Anpec (trade name), Dainippon Pharmaceutical Co., Ltd.) to induce defecation dysfunction and then the stool weight was measured to evaluate the acceleratory effect of GM-611 on defecation in the model. Rabbits (Kbl:JW) were subcutaneously administered with vehicle (physiological saline) or morphine (1 mg/kg) and fed for 30 minutes (feeding stimulation), followed by oral administration of vehicle (3 w/v % gum arabic suspension) or GM-611 at a dose of 1.25 mg/kg, 2.5 mg/kg, 5 mg/kg, 10 mg/kg or 20 mg/kg. The stool weight for 2.5 hours after administration was measured (11 rabbits in each group) to examine the improving effect of GM-611 on morphine-induced defecation dysfunction.

[Results]

Figure 5:
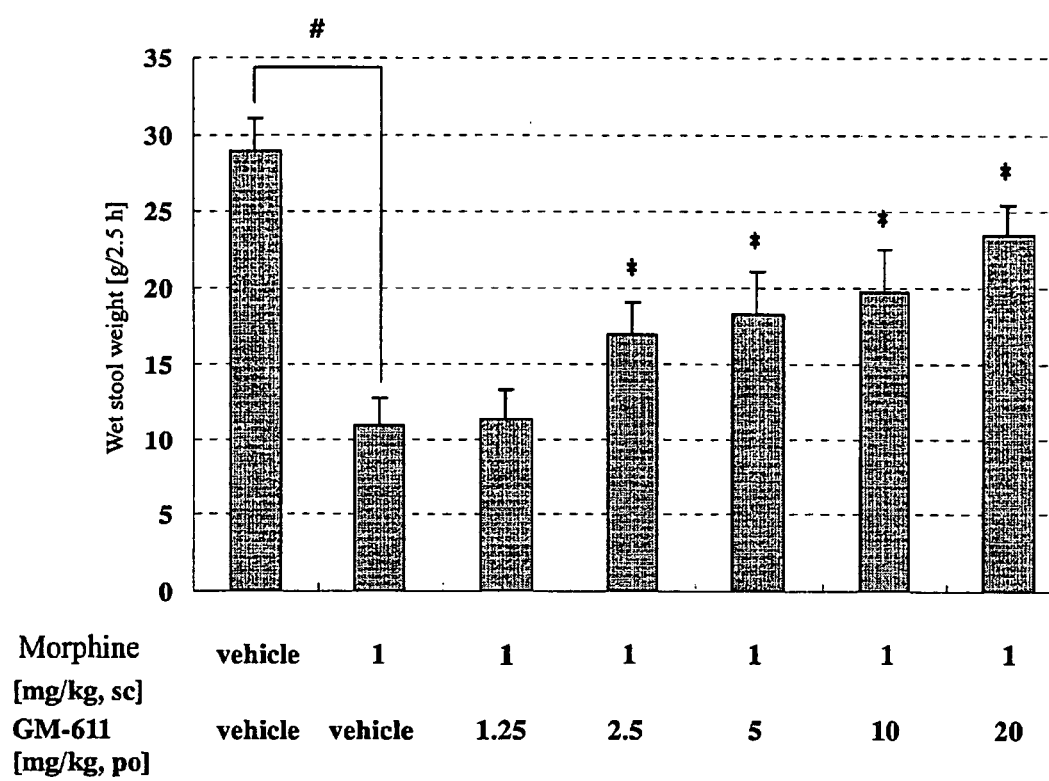
FIG. 5 shows an example of the results, in which the stool weight was measured for each morphine-induced defecation dysfunction rabbit administered with the therapeutic and/or preventive agent for defecation dysfunction according to the present invention.

The results obtained are shown in FIG. 5 (#P<0.05 by Student's t-test, *P<0.05 vs morphine (1 mg/kg)-treated group by Williams' test). It was shown that defecation dysfunction was caused in this model, because morphine significantly inhibited defecation enhanced by feeding stimulation. GM-611 dose-dependently improved morphine-induced defecation dysfunction, and the stool weight at the maximum dose of GM-611 (20 mg/kg) reached the same level as observed in the morphine-untreated group without defecation dysfunction. These results showed that GM-611 had the improving effect on defecation dysfunction.

Example 3

Acceleratory Effect of GM-611 on Defecation in Normal Dogs

In addition to the studies in rabbits, the acceleratory effect of GM-611 on defecation was also studied in normal dogs. Five beagle dogs were each catheterized to insert an intragastric catheter (Chugai Pharmaceutical Co., Ltd., 8.3-9.9 kg, 2 males and 3 females). Each dog was fed with pellets (CD-5 (CLEA Japan, Inc.), about 250 g) at 9:00 a.m. and then monitored for its defecation immediately after feeding. One hour after feeding, the animals having defecation within 1 hour were intragastrically administered via the catheter with vehicle (3 w/v % gum arabic suspension) or GM-611 (0.3 mg/kg, 1 mg/kg, 3 mg/kg) and then measured for the time until the first defecation after administration.

[Results]

Figure 6:
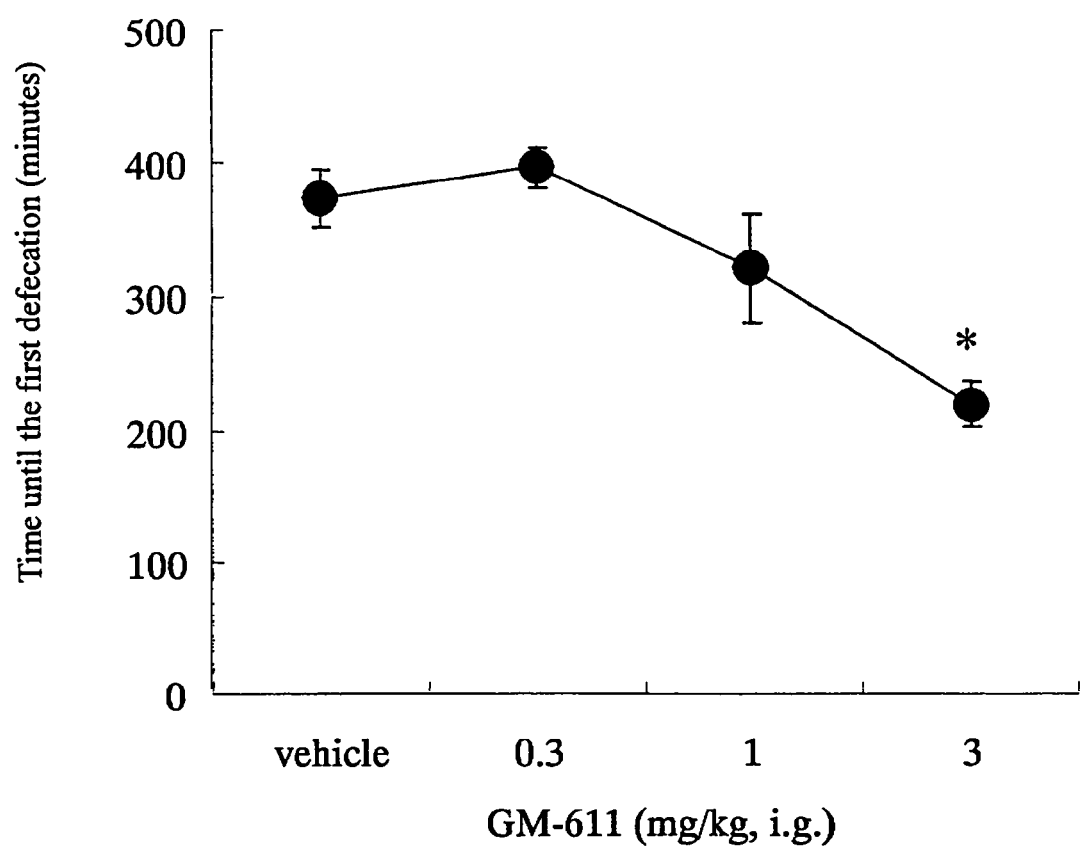
FIG. 6 shows an example of the results, in which the time until the first defecation was measured for each dog administered with the therapeutic and/or preventive agent for defecation dysfunction according to the present invention.

The results obtained are shown in FIG. 6 (*P<0.05 vs vehicle group by Dunnett's test, n=5). GM-611 dose-dependently decreased in the time until the first defecation after administration. Moreover, stool condition at that time was not diarrhea. These results showed that GM-611 also had the acceleratory effect on defecation in dogs.

Example 4

Acceleratory Effect of GM-611 on Defecation in Healthy Volunteers

The acceleratory effect of GM-611 on defecation was studied by repeated oral administration of GM-611 in Phase I trials. Healthy male volunteers, in groups of 6, were orally administered for 10 days with placebo or GM-611 (5 mg, 10 mg, 20 mg) on a three-times-a-day basis together with 150 mL water at 30 minutes before each meal, provided that the volunteers were administered once before breakfast on the first and tenth days. The volunteers were then monitored for their defecation during the period of administration. The acceleratory effect on defecation was assessed by the daily frequency of defecation, the number of days that at least one defecation was observed (the number of defecation days), and stool condition (watery diarrhea, muddy diarrhea, muddy soft stool, formed soft stool, normal stool, hard stool, very hard stool). It should be noted that in this test, the subjects were allocated at random to each test group and tested in a double-blind manner.

[Results]

Figure 7:
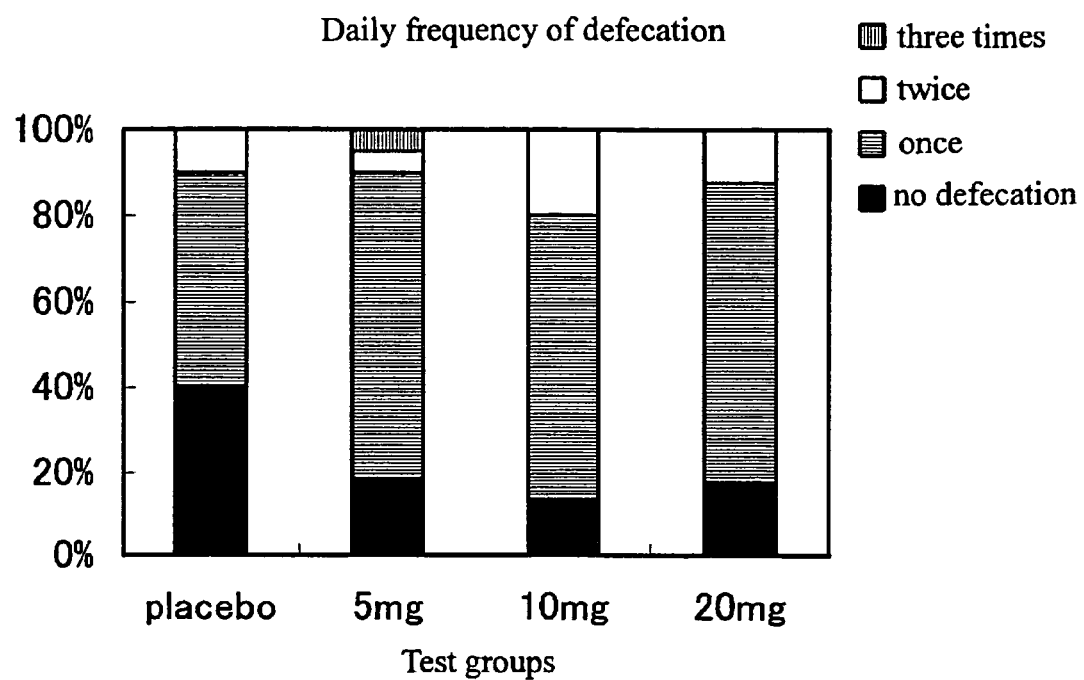
FIG. 7 shows an example of the results, in which the change in daily frequency of defecation was measured for each healthy volunteer administered with the therapeutic and/or preventive agent for defecation dysfunction according to the present invention.

The results obtained are shown in FIG. 7. When the number of defecation days was compared between the GM-611-treated groups (5, 10 and 20 mg groups) and the placebo-treated group, the average number of defecation days was 6.0 in the placebo-treated group, whereas it was 8.2 when averaged over all the GM-611-treated groups. Thus, the GM-611-treated groups showed a significant increase in the number of defecation over the placebo-treated group (p=0.012). Likewise, the average daily frequency of defecation was 0.7 in the placebo-treated group, whereas it was 1.0 in the GM-611-treated groups, indicating that the frequency of defecation tended to be higher in the GM-611-treated groups than the placebo-treated group. In contrast, there was no change in stool condition between the placebo-treated group and the GM-611-treated groups. These results suggested that GM-611 accelerated defecation in healthy volunteers (male) without changing stool into a diarrheal form.

INDUSTRIAL APPLICABILITY

As shown in the above examples, the inventors of the present invention found for the first time that an erythromycin derivative of Formula (1) had an improving effect on defecation dysfunction and clinically exerted the effect in humans. It was also found that this improving effect on defecation dysfunction led to stimulation of normal defecation, unlike a laxative. Further, the compound of Formula (1) according to the present invention is also suitable for long-term clinical use because of its weaker antibacterial action than erythromycin. In view of the foregoing, the present invention provides an agent having a safe and potent therapeutic and/or preventive effect on defecation dysfunction.

The invention claimed is:

1. A method for treating constipation in a patient with constipation, which comprises
   administering to the patient, a therapeutic agent for constipation, which comprises as an active ingredient a compound of Formula (1) or a pharmaceutically acceptable salt thereof:

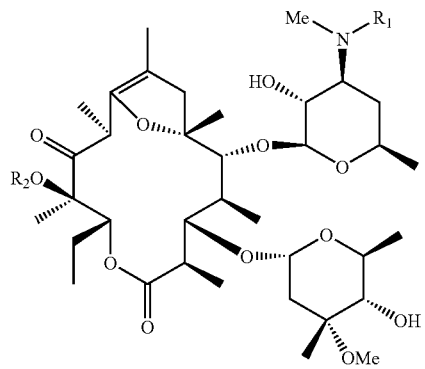

wherein $R_1$ represents an isopropyl group and $R_2$ represents a methyl group, in doses sufficient to treat constipation in the patient.

2. The method according to claim 1, wherein the constipation is analgesic-induced constipation, or induced morphine-induced constipation.

3. The method according to claim 1, wherein the constipation is functional constipation.

4. The method according to claim 1, wherein the constipation is constipation associated with irritable bowel syndrome, atonic constipation, rectal constipation or chronic constipation.

5. The method according to claim 1, wherein the constipation is senile constipation.

6. The method according to claim 1, which accelerates normal defecation.

* * * * *